United States Patent [19]
Dyken et al.

[11] Patent Number: 6,093,202
[45] Date of Patent: Jul. 25, 2000

[54] THERAPEUTIC COLD AND HEAT PACK SYSTEM

[76] Inventors: Kathryn E. Dyken; Jack A. Dyken, both of 923 St. Paul Dr. #155, Richardson, Tex. 75080

[21] Appl. No.: 09/396,892

[22] Filed: Sep. 15, 1999

[51] Int. Cl.[7] .................................................... A61F 7/00
[52] U.S. Cl. ......................... 607/109; 607/108; 607/112
[58] Field of Search ............................... 607/109, 96, 108, 607/110, 112, 114; 606/27; 381/370, 374, 376

[56] References Cited

U.S. PATENT DOCUMENTS

| | | | |
|---|---|---|---|
| 3,796,855 | 3/1974 | Brown et al. ............................ | 219/211 |
| 5,353,605 | 10/1994 | Naaman ................................... | 62/259.3 |
| 5,456,703 | 10/1995 | Beeuwkes, III ........................ | 607/109 |
| 5,716,388 | 2/1998 | Petelle .................................... | 607/108 |
| 5,809,573 | 9/1998 | Bary ....................................... | 2/209 |
| 5,837,004 | 11/1998 | Lavore .................................... | 607/109 |
| 5,984,951 | 11/1999 | Weiss et al. ............................ | 607/109 |

*Primary Examiner*—Linda C. M. Dvorak
*Assistant Examiner*—Jocelyn Ram
*Attorney, Agent, or Firm*—Rudolf O. Siegesmund

[57] ABSTRACT

A gel pad and gel pad system for application of heat or cold to various parts of a human body through the use of a pad and headpiece, pad and strap or a combination of pad, headpiece, pad and strap.

11 Claims, 4 Drawing Sheets

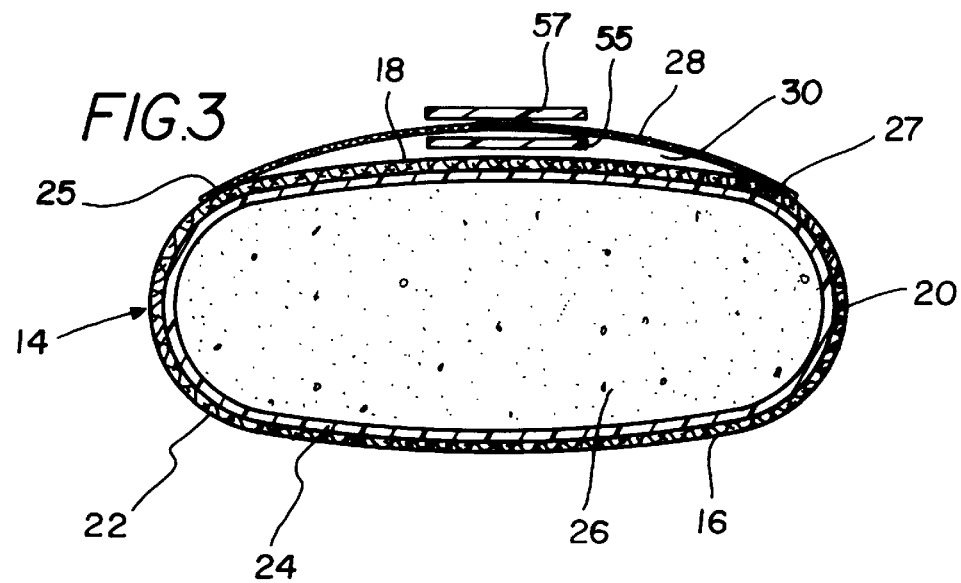
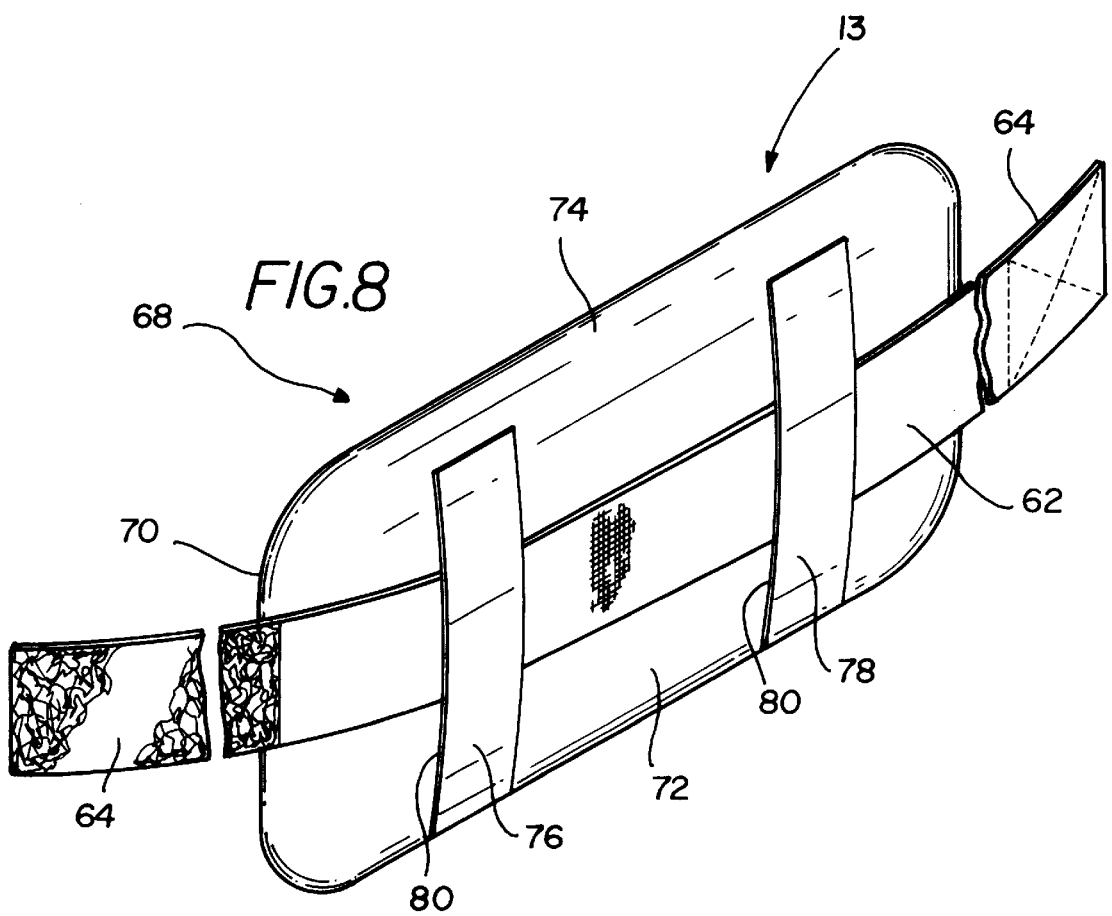

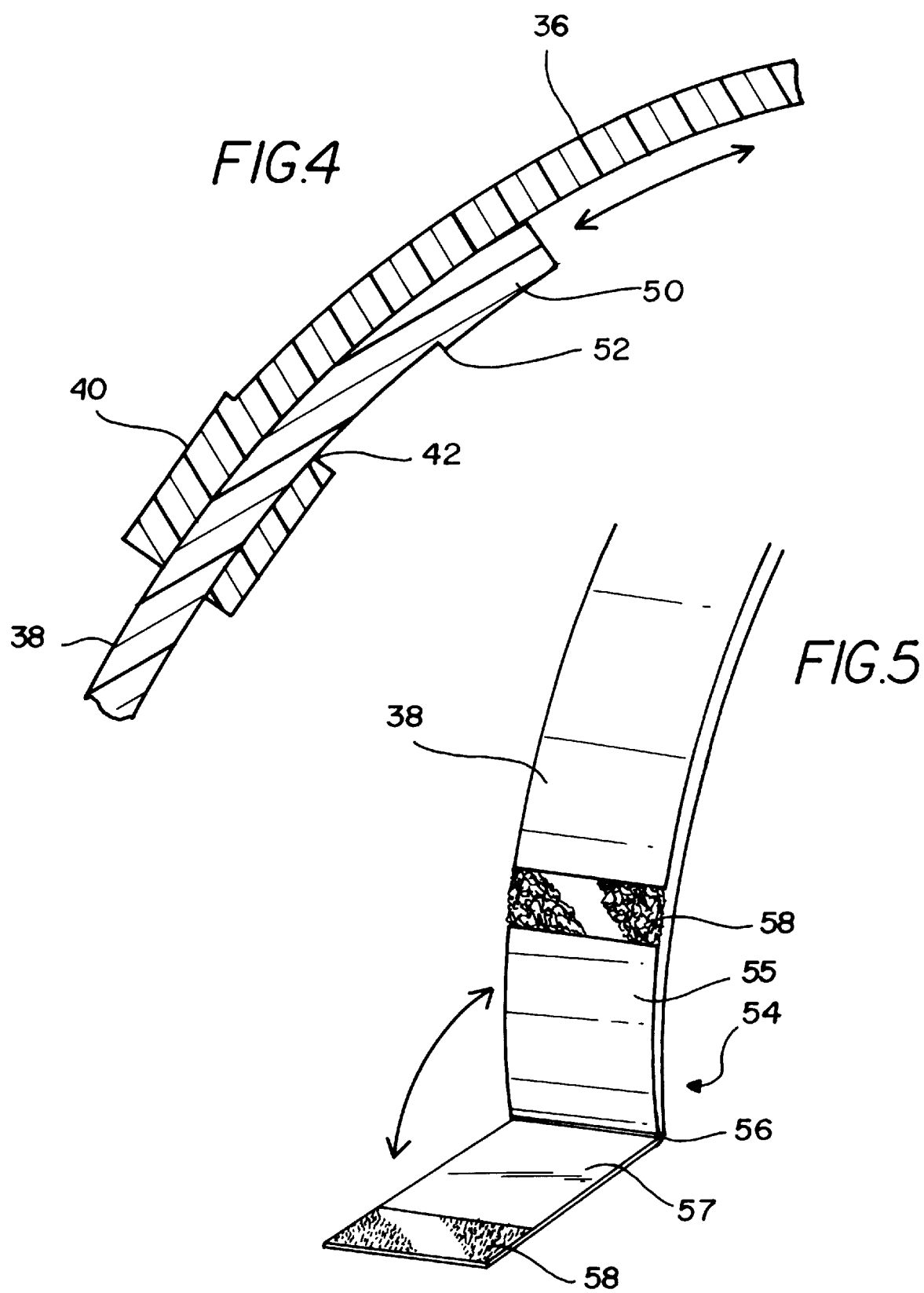

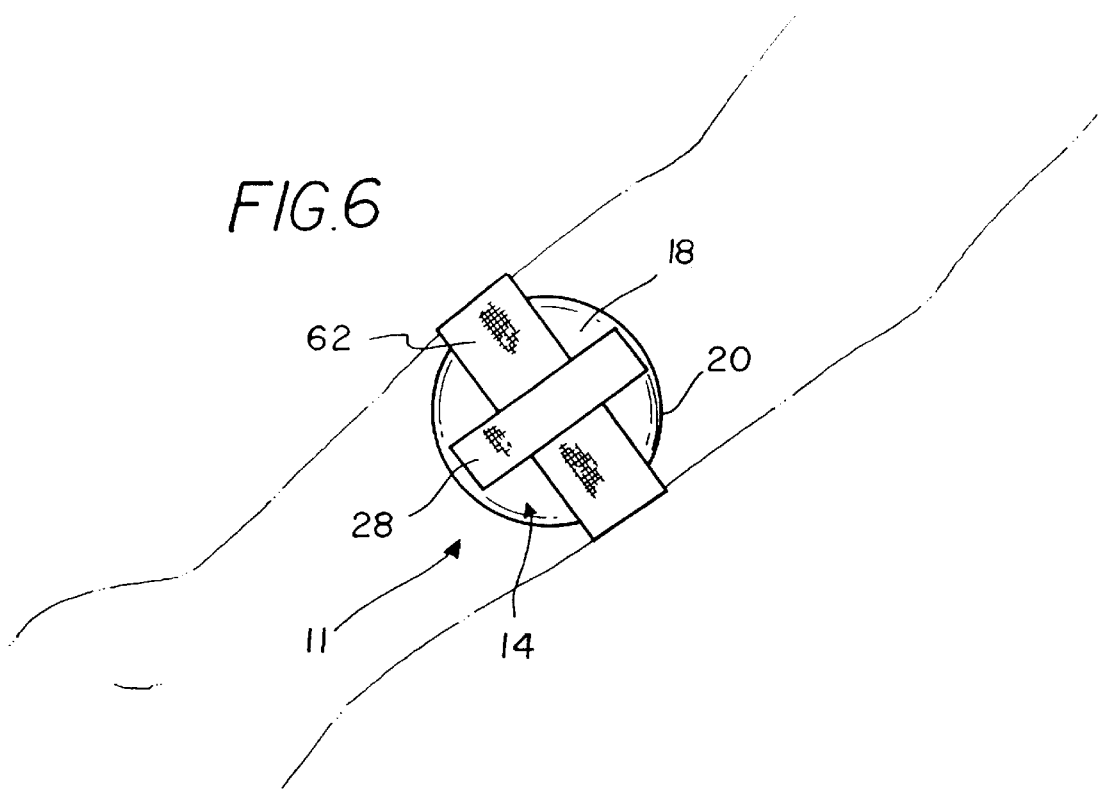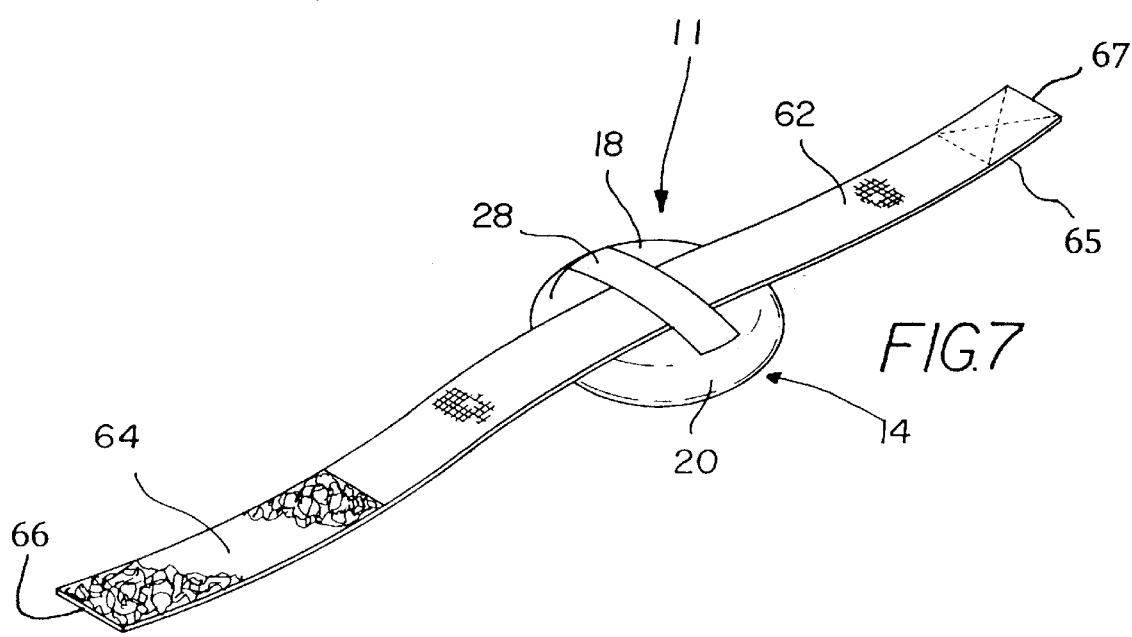

THERAPEUTIC COLD AND HEAT PACK SYSTEM

BACKGROUND OF THE INVENTION

1. Field of the Invention

The present invention relates to medical therapy devices and more particularly to a system of heated or chilled gel packs for positioning against different parts of a human body.

2. Description of the Prior Art

The use of medical therapy devices that employ the use of chilled or heated gel packs, along with their attendant attachment structures, is known in the prior art. For example, U.S. Pat. No. 5,393,462, issued to Avery on Feb. 28, 1995, discloses a refrigerant gel pad for heating or cooling portions of a person's body. The '462 patent is silent on how the gel pad would be attached to the body.

A typical attachment structure for use with a refrigerant gel pack is shown in U.S. Pat. No. 5,409,500, issued to Dyrek on Apr. 25, 1995. In the '500 patent, a therapeutic cold pack filled with a refrigerant gel, is attached to the body by straps having hook and loop fasteners. Similarly, U.S. Pat. No. Des. 383,547, issued to Mason et al. on Sep. 9, 1997, discloses an ornamental design for a cold therapy pad with hook and loop fasteners.

While all of the therapeutic devices disclosed in the above discussed patents fulfill their respective intended purposes, a need exists beyond these patents for a system of gel pads that can be applied to various parts of the body including difficult areas such as the ear. A further need exists for a comfortable way to affix the pads to the body. More particularly, in order to effectively secure a therapeutic pad in any type of secure and useful position on a person's body, conventional hook and loop fastener type straps must be tightened to such a degree as to become painfully uncomfortable. The pain is even more pronounced when these straps are positioned around muscles and other parts of the person's body which normally contract and expand, thereby continually varying the intensity of the tightness.

Therefore, a need exists for gel pad system that can be used on different parts of the body and that can be secured by attachment straps that expand and contract with the movement of the body. A need exists for a gel pad system that will allow a person to wear the gel pads while working and to be mobile and active while receiving the benefit of the heat or cold. A further need exists for gel pads that can be inexpensively manufactured while being durable and reliable.

SUMMARY OF THE INVENTION

The present invention meets the needs identified above by providing a therapeutic gel pad system with components that can be configured to apply cold or heat therapy to different parts of a human body securely and without discomfort. One component of the system is a round therapeutic gel pack held against a user's ear through the use of a detachable flexible headpiece. The same round therapeutic gel pack can be affixed to an arm or leg by removing the detachable flexible headpiece and inserting a flexible, stretchable and adjustable strap. Finally, using the stretchable and adjustable strap, a larger rectangular pad can be affixed to the body for coverage of larger areas such as the back.

The foregoing and other objects, features and advantages of the invention will be apparent from the following more particular description of a preferred embodiment of the invention, as illustrated in the accompanying drawings wherein like reference numbers represent like parts of the invention.

BRIEF DESCRIPTION OF THE DRAWINGS

FIG. 3 is a cross-sectional view of the round pad along line 3—3 in FIG. 1.

FIG. 4 is a cross-sectional view of the band along line 4—4 in FIG. 1.

FIG. 5 is a partial perspective view of the connector portion of the band.

FIG. 6 is a plan view of a the pad with strap.

FIG. 7 is a perspective view of the p ad with strap.

FIG. 8 is a perspective view of a rectangular pad with strap.

DESCRIPTION OF PREFERRED EMBODIMENTS

Figure 1:
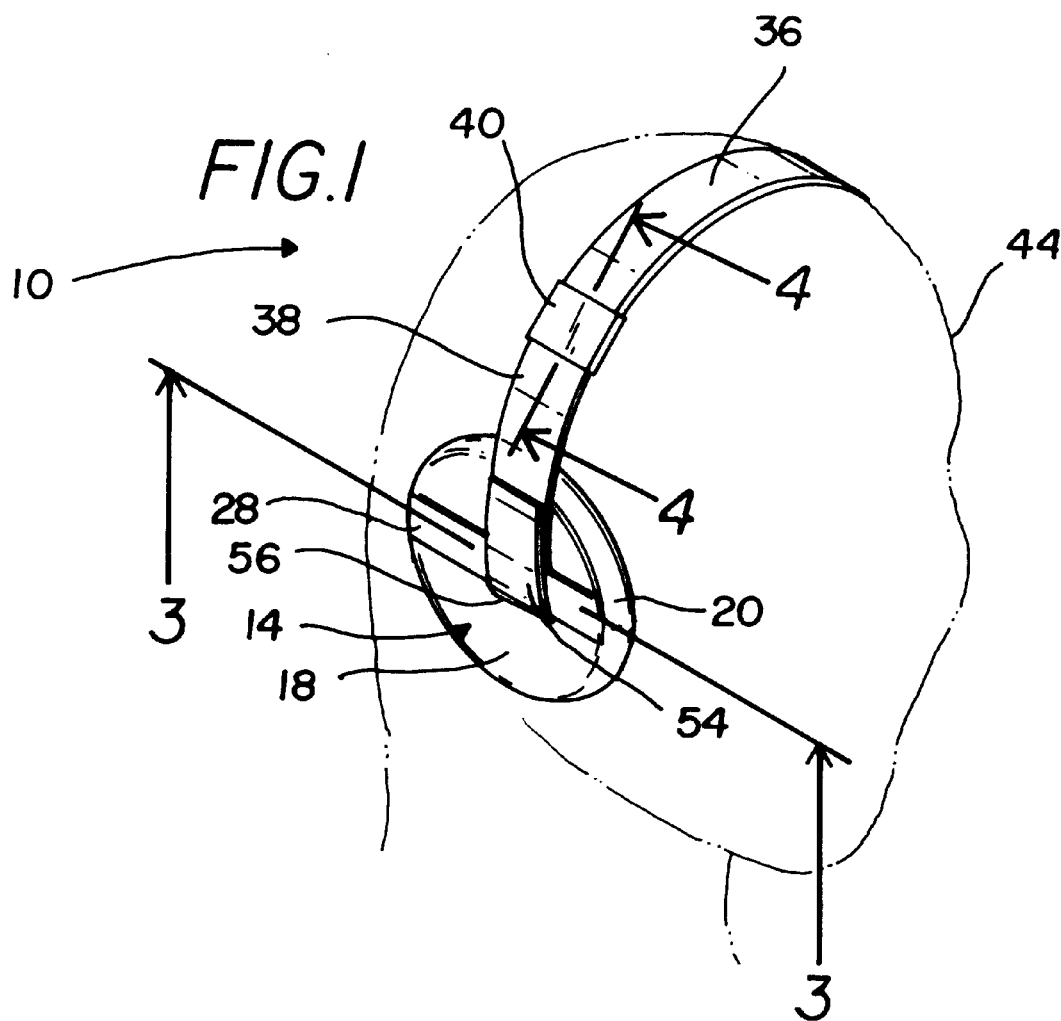
FIG. 1 is a left side perspective view of the round pad with band.

In FIG. 1, first gel pad assembly 10 includes first pad 14 having a generally planar, circular configuration and inner face 16, outer face 18, rounded peripheral edge 20. Cross section 3—3 of FIG. 1 is illustrated in FIG. 3. Referring to FIG. 3, first pad 14 comprises cover 22 which encapsulates first pad 14, and lining 24 attached to cover 22. In the preferred embodiment cover 22 is made of cloth and lining 24 is made of plastic. Gel 26 is adapted to be selectively heated and cooled by conventional means, and is sealed within lining 24. As used herein the term gel means a semi-rigid colloidal dispersion of a solid within a liquid which retains heat or cold depending on the temperature to which the gel has been subjected. Short strip 28 has short strip first end 25 fixedly engaged to outer face 18 and short strip second end 27 fixedly engaged to outer face 18, and short strip 28 extends across outer face 18. Short strip 28, when affixed to outer face 18, defines opening 30 between short strip 28 and outer face 18. In an alternative embodiment, short strip first end 25 and short strip second end 27 have hook and loop fasteners (not shown) allowing selective tensioning of short strip 28 to outer face 18.

Figure 2:
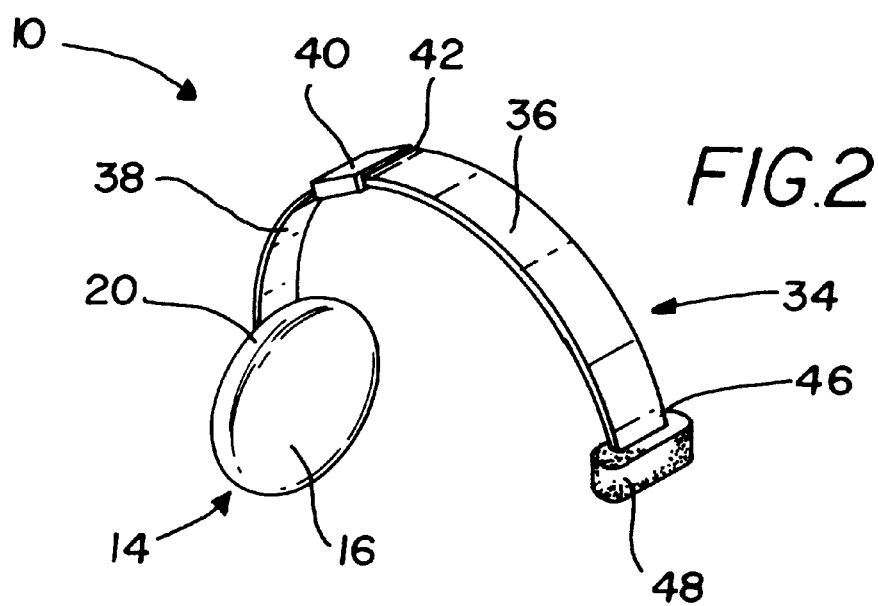
FIG. 2 is a right side perspective view of the round pad with band.

FIG. 2 provides an overview of first gel pad assembly 10 assembled and ready for use and adjustment. In FIG. 2 first gel pad assembly is viewed from the opposite direction of FIG. 1. Gel pad assembly 10 has first pad 14, first band segment 36 and second band segment 38.

In FIG. 4, headband assembly 34 has first band segment 36 slidably attached to second band segment 38. First band segment 36 has first band interior end 40 and first band exterior end 46. First band interior end 40 has slot 42. First band exterior end 46 is formed to receive padded member 48 positioned adjacent to head 44. Padded member 48 is removable so that various sizes of padded member 48 can be interchanged in order to vary the gripping tension of headband assembly 34. Second band segment 38 has protrusion 52 fixedly engaged to second band interior end 50. Protrusion 52 prevents second band segment 38 sliding all the way through slot 42 in first band interior end 40. Second band interior end 50 is inserted through slot 42 of first band segment 36, thereby allowing first band segment 36 and second band segment 38 to slide with respect to each other. Second band segment 38 also has second band distal end 54 defined by tapered section 55 and second band planar section 57. Flexible hinge 56 operates to rotatably connect first tapered section 55 and second tapered section 57 together. First tapered section 55 narrows at flexible hinge 56 and can be manually bent changing the shape of headband assembly 34 to achieve a better fit to head 44.

First fastener 58 is affixed to second band segment 38 and second fastener 59 is affixed to second tapered section 57 so that when first tapered section 55 is rotated about flexible hinge 56 first fastener 58 will engage second fastener 59. First fastener 58 and second fastener 59 hook and loop type fasteners. As used herein, hook and loop type fasteners include but are not limited to Velcro type micro loop texture fasteners Second band distal end 54 is intended to be removably inserted through opening 30 defined by short strip 28 of first pad 14, and is secured by inserting first tapered section 55 through opening 30 and rotating first tapered section 55 about flexible hinge 56 until first fastener 58 engages second fastener 59 securing second band segment 38 to first pad 14. First fastener 58 and second fastener 59 may be varied in size to encompass sufficient surface area of first tapered section 55 and second tapered section 57 to ensure that first fastener 58 and second fastener 59 will stay connected so that first pad 14 remains affixed to headband assembly 34. Manual pressure can be applied to separate first fastener 58 and second fastener 59 so that headband assembly 34 can be removed from first pad 14.

Size adjustment and tensioning of first gel pad assembly 10 relative to head 44 can be achieved by five different adjustments. First, first band segment 36 can be slid in relation to second band segment 38 and the relative position of first band segment 36 to second band segment 38 maintained by frictional engagement. Second, first fastener 58 and second fastener 59 can be engaged and disengaged to allow positioning of first pad 14 relative to short strip 28. Third, first tapered section 55 can be bent and deformed to change its position due to first tapered sections tapered width. Fourth, opening 30 can be made larger or smaller by changing the tension of short strip 28 relative to first pad 14 by changing the location where short strip first end 25 is fixedly engaged to outer face 18 and short strip second end 27 is fixedly engaged to outer face 18. Fifth, different sizes of padded member 48 may be affixed to first band exterior end 46.

First band segment 36 and second band segment 38 may be formed from suitable semi-rigid material with an elasticity sufficient enough to hold headband assembly 34 and first pad 14 against head 44. Inner surface 16 of first pad 14 is in direct contact with the user's skin to provide cooling or heating as required for medical purposes.

In FIG. 6, second gel pack assembly 11 is shown. Second gel pack assembly 11 may be retained against a user's body by strap 62, wherein the strap 62 is elastic. First pad 14 is the same as first pad 14 in FIGS. 1 and 2.

Referring to FIG. 7, strap 62 has strap first end 66 with strap first fastener 64 attached and strap second end 67 with strap second fastener 65 attached. Either strap first end 66 or strap second end 67 may be inserted through the opening defined by short elongated strip 28 of refrigerant first pad 14, and strap 62 can then be wrapped around a user's limb and secured by bringing strap first end 66 with strap first fastener 64 attached into contact with strap second end 67 with strap second fastener 65 attached so that strap first fastener 64 and strap second fastener 65 are engaged. In the preferred embodiment, strap first fastener 64 and strap second fastener 65 are hook and loop fasteners. Persons of ordinary skill in the art will be aware of different methods of removably engaging strap first end 66 and strap second end 67.

In FIG. 8 third gel pack assembly 13 has second pad 68 having a generally rectangular configuration and inner face 70, outer face 72, and peripheral rounded edge 74. Although not shown, second pad 68 is constructed in the same manner as first pad 14 as depicted in FIG. 3. Only the outer configuration of second pad is different. Second pad first strip 76 and second pad second strip 78 may be permanently or removably attached at their ends to outer face 70 of second pad 68 with second pad first strip 76 and second pad second strip 78 lying in parallel alignment with each other, thereby defining second opening 80 and third opening 81 between second pad first strip 76 and second pad second strip 78 respectively with outer face 72 of second pad 68. Strap 62 has strap first end 66 with strap first fastener 64 attached and strap second end 67 with strap second fastener 65 attached. Either strap first end 66 or strap second end 67 may be inserted through second opening 80 and third opening 81 defined by first short strip 76 and second short strip 78, and strap 62 can then be wrapped around a limb of a user's body and secured thereto by affixing strap first fastener 64 to strap second fastener 65. By using additional straps (not shown) similar to strap 62 but of varying lengths, an additional strap can be attached to strap 62 to allow second pad 68 to be affixed to an area requiring a longer strap such as the back or shoulder.

In summary, it can be seen that gel pack assembly 10, gel pack assembly 11 and gel pack assembly 13 of the present invention allow first pad. 14 and second pad 68 to be applied simultaneously and held against selected areas of a user's body, thereby providing an apparatus and method for portable treatment of concurrent ailments such as earaches, headaches, muscular pains, and other similar medical conditions.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

We claim:

1. An apparatus comprising:
    a first pad having a first pad strip fixedly or removably attached to said pad; and
    a headpiece comprising a first section and a second section slidingly engaged to said first section, said second section further comprising a first tapered section with a first securement device and a second tapered section with a second securement device;
    wherein, when said second tapered section passes between the first pad strip and the first pad and is rotated so that the second securement device fixedly and removably engages the first securement device said headpiece is removably attached to said first pad.

2. The first pad of claim 1 further comprising a strip with a first end and a second end, said first end of said strip fixedly or removably engaged to said first pad and said second end of said strip fixedly or removably engaged to said first pad.

3. The apparatus of claim 1, wherein said first pad further comprises a gel, a liner and a cover.

4. The apparatus of claim 1 wherein said first securement device and said second securement device comprise hook and loop fasteners.

5. The headpiece of claim 1 farther comprising a padded member removably attached to said headpiece.

6. A gel pad system comprising:

a first pad having a strip with a first end fixedly or removably engaged to said first pad and a second end fixedly or removably engaged to said first pad;

a headpiece having a first section and a second section slidingly engaged to said first section, said second section further comprising a first tapered section with a first securement device and a second tapered with a second securement device;

wherein, when said second tapered section passes between the strip and the first pad and is rotated so that the second securement device fixedly and removably engages the first securement device said first pad is fixedly and removably engaged to said headpiece;

one or more straps each having a strap first end and a strap second end;

wherein each said strap first end has a third securement device fixedly attached thereto and each said strap second end has a fourth securement device fixedly attached thereto;

a second pad having at least two second pad straps affixed thereto for receiving each said strap whereby when said third securement device contacts said fourth securement device, said strap first end and said strap second end are fixedly and removably engaged.

7. The gel pad system of claim 6, wherein said first pad further comprises a gel, a liner and a cover.

8. The gel pad system of claim 6, wherein the second pad further comprises a gel, a liner and a cover.

9. The gel pad system of claim 6 wherein said first securement device, said second securement device, said third securement device and said fourth securement device comprise hook and loop fasteners.

10. The headpiece of claim 6 further comprising a padded member removably attached to said first section of said headpiece.

11. A gel pad system comprising:

a first pad having a first pad strip with a first end and a second end, said first end of said strip fixedly or removably engaged to said first pad and said second end of said strip fixedly or removably engaged to said first pad, said first pad further comprising a gel, a liner, a padded member and a cover;

a headpiece having a first section and a second section slidingly engaged to said first section, said second section further comprising a first tapered section with a first securement device and a second tapered with a second securement device;

one or more straps each having a strap first end and a strap second end;

a second pad having at least two second pad straps affixed thereto for receiving said strap, said second pad comprising a gel, a liner, a padded member and a cover;

wherein, when said second tapered section passes between the first pad strip and the first pad and is rotated so that the second securement device fixedly and removably engages the first securement device said headpiece is removably attached to said first pad;

wherein said strap first end has a third securement device fixedly attached thereto and said strap second end has a fourth securement device fixedly attached thereto;

whereby when said third securement device contacts said fourth securement device, said strap first end and said strap second end are fixedly and removably engaged;

wherein said first securement device, said second securement device, said third securement device and said fourth securement device comprise hook and loop fasteners.

* * * * *